(12) United States Patent
Chen

(10) Patent No.: US 7,762,839 B2
(45) Date of Patent: Jul. 27, 2010

(54) PATCH PANEL ASSEMBLY

(75) Inventor: Chou-Hsing Chen, Keelung (TW)

(73) Assignee: Surtec Industries, Inc., Keelung (TW)

( * ) Notice: Subject to any disclaimer, the term of this patent is extended or adjusted under 35 U.S.C. 154(b) by 25 days.

(21) Appl. No.: 12/341,127

(22) Filed: Dec. 22, 2008

(65) Prior Publication Data

US 2010/0159742 A1    Jun. 24, 2010

(51) Int. Cl.
*H01R 13/60* (2006.01)
(52) U.S. Cl. .................................. 439/540.1
(58) Field of Classification Search .............. 439/540.1, 439/676, 941, 620
See application file for complete search history.

(56) References Cited

U.S. PATENT DOCUMENTS

| | | | |
|---|---|---|---|
| 5,700,167 A * | 12/1997 | Pharney et al. .............. | 439/676 |
| 6,086,415 A | 7/2000 | Sanchez et al. | |
| 6,273,752 B1 | 8/2001 | Martin et al. | |
| 6,504,726 B1 | 1/2003 | Grabinger et al. | |
| 6,736,670 B2 | 5/2004 | Clark et al. | |
| 6,918,786 B2 * | 7/2005 | Barker et al. ............. | 439/540.1 |
| 7,343,078 B2 | 3/2008 | Spisany et al. | |
| 7,488,205 B2 * | 2/2009 | Spisany et al. ........... | 439/540.1 |
| 2005/0191901 A1 * | 9/2005 | Follingstad ................. | 439/534 |

* cited by examiner

*Primary Examiner*—Jean F Duverne
(74) *Attorney, Agent, or Firm*—McGlew and Tuttle, P.C.

(57) ABSTRACT

A patch panel assembly is provided including an angle module having one or more RJ modules, one or more insulation displacement contact (IDC) modules and a printed circuit board. Each of the RJ modules includes a base, an RJ plug receiving opening and spring contacts extending from the base into the RJ plug receiving opening. The IDC modules each include an IDC housing with an IDC module base and insulation displacement contacts (IDCs) with IDC contact pins extending from the IDC module base. The printed circuit board has RJ contact holes receiving the spring contacts with the RJ module mounted to the printed circuit board and has IDC contact holes receiving the IDC contact pins with the IDC module mounted to the printed circuit board as well as circuit traces connecting the RJ contact holes to the IDC contact holes. The plug receiving openings each have a plug insertion opening at an angle to the printed circuit board between to 0° and not equal to 90°. A front panel is provided including a front face with a plurality of RJ module openings. The angle module is connected to the frame with the one or more RJ modules extending through RJ module openings and with each the plug insertion opening at an angle to the front face between 0° and 90°.

10 Claims, 15 Drawing Sheets

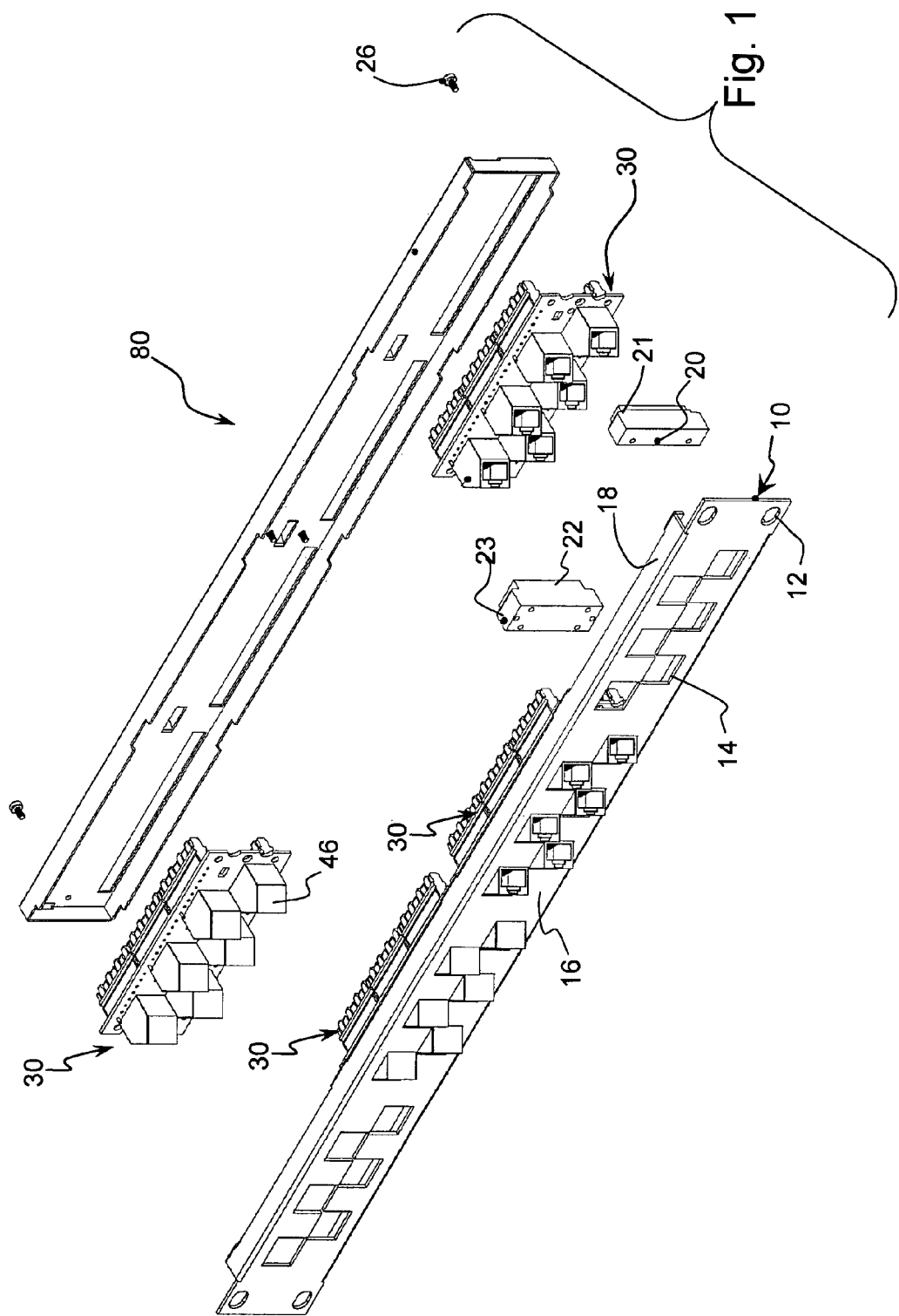

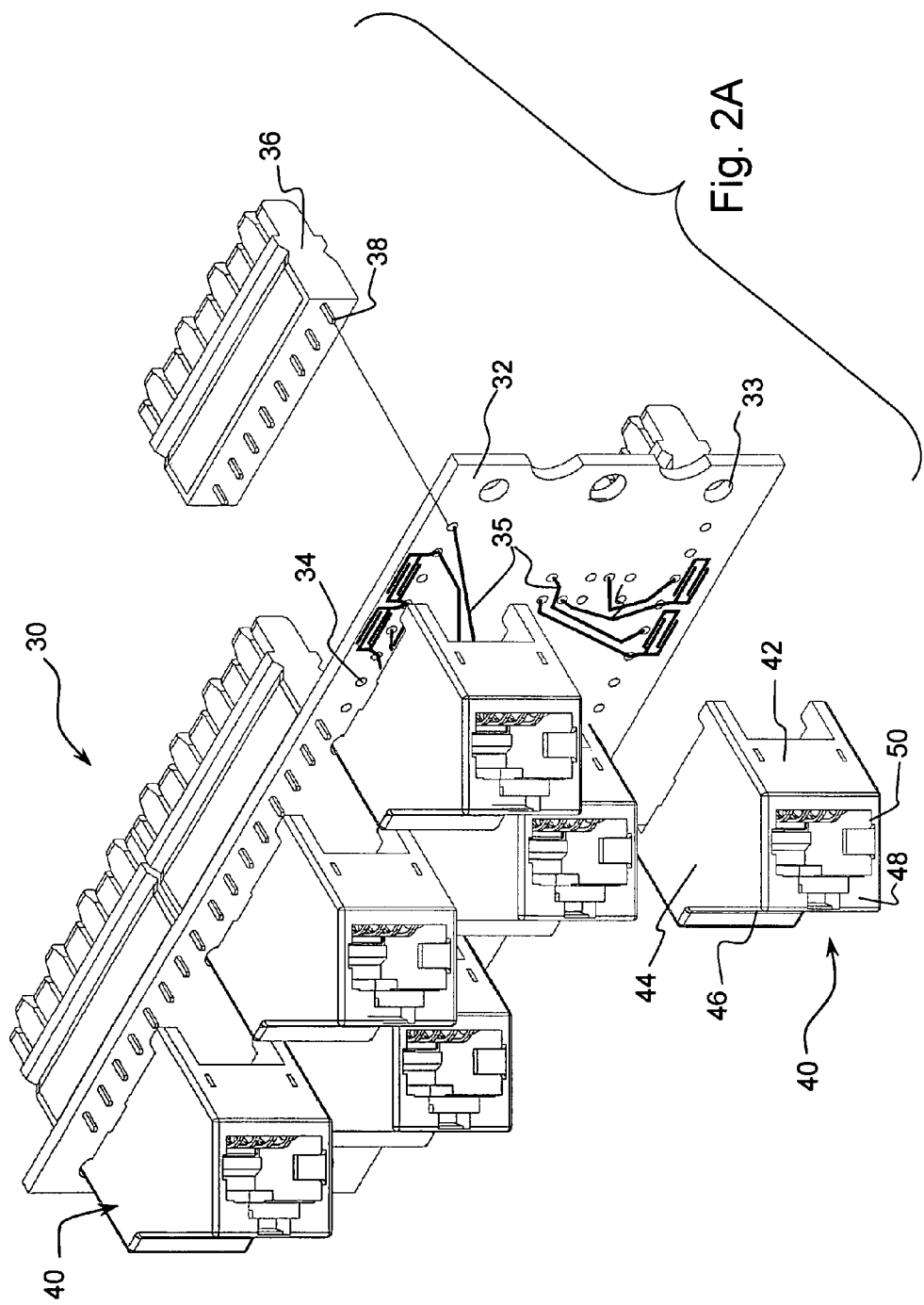

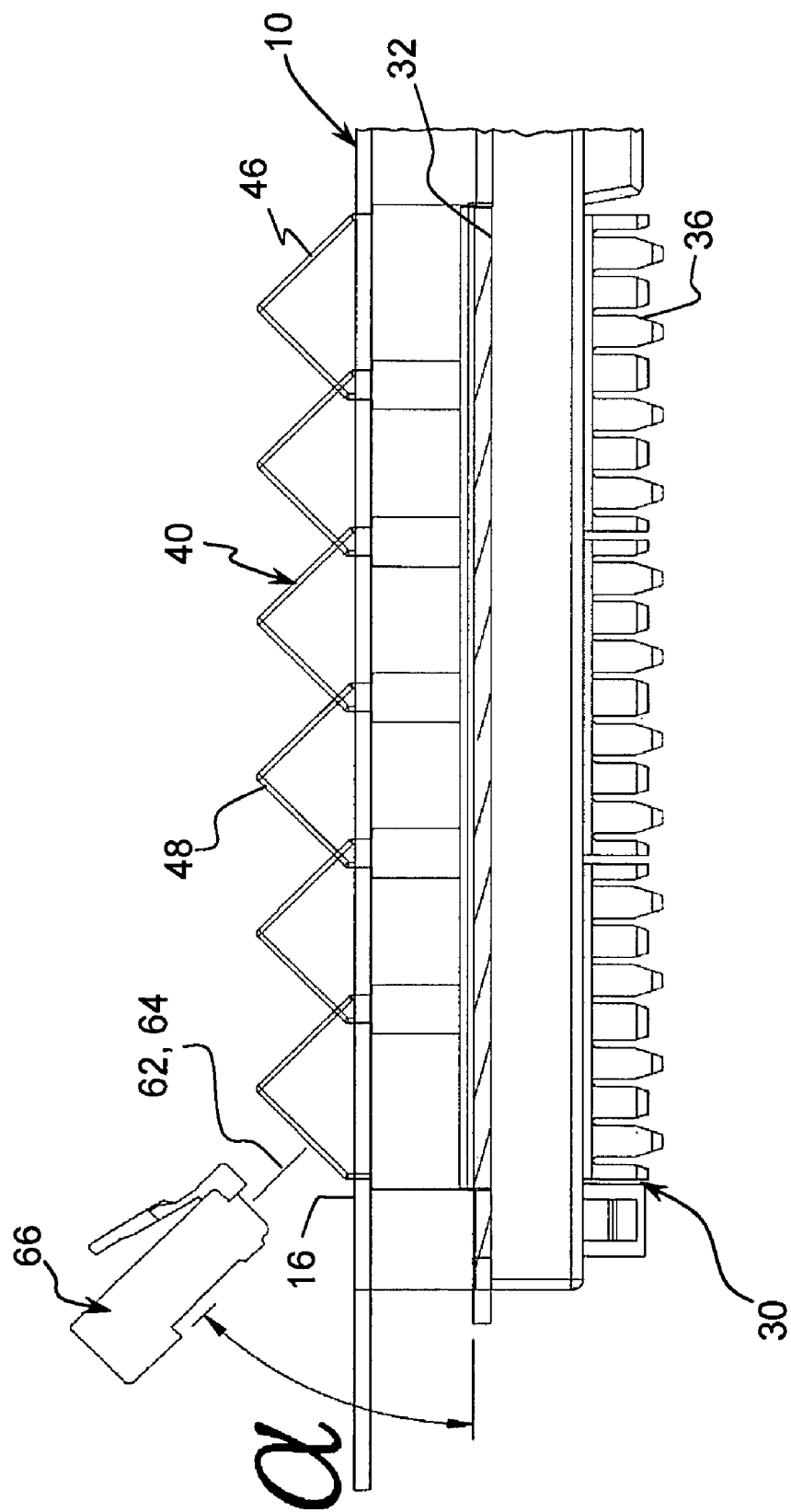

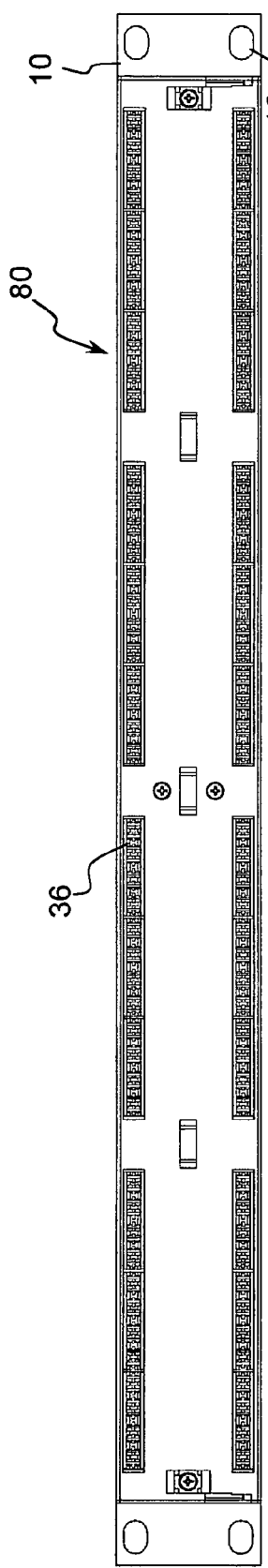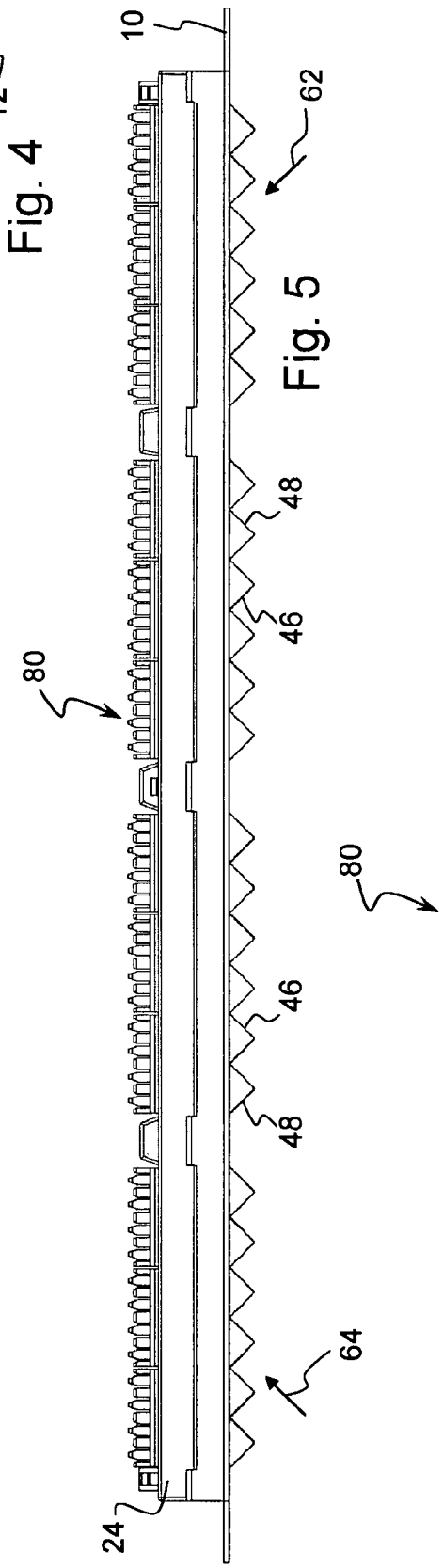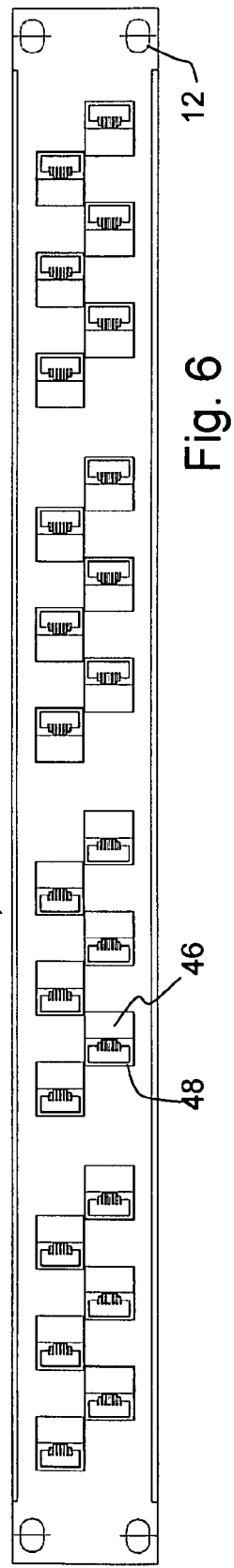

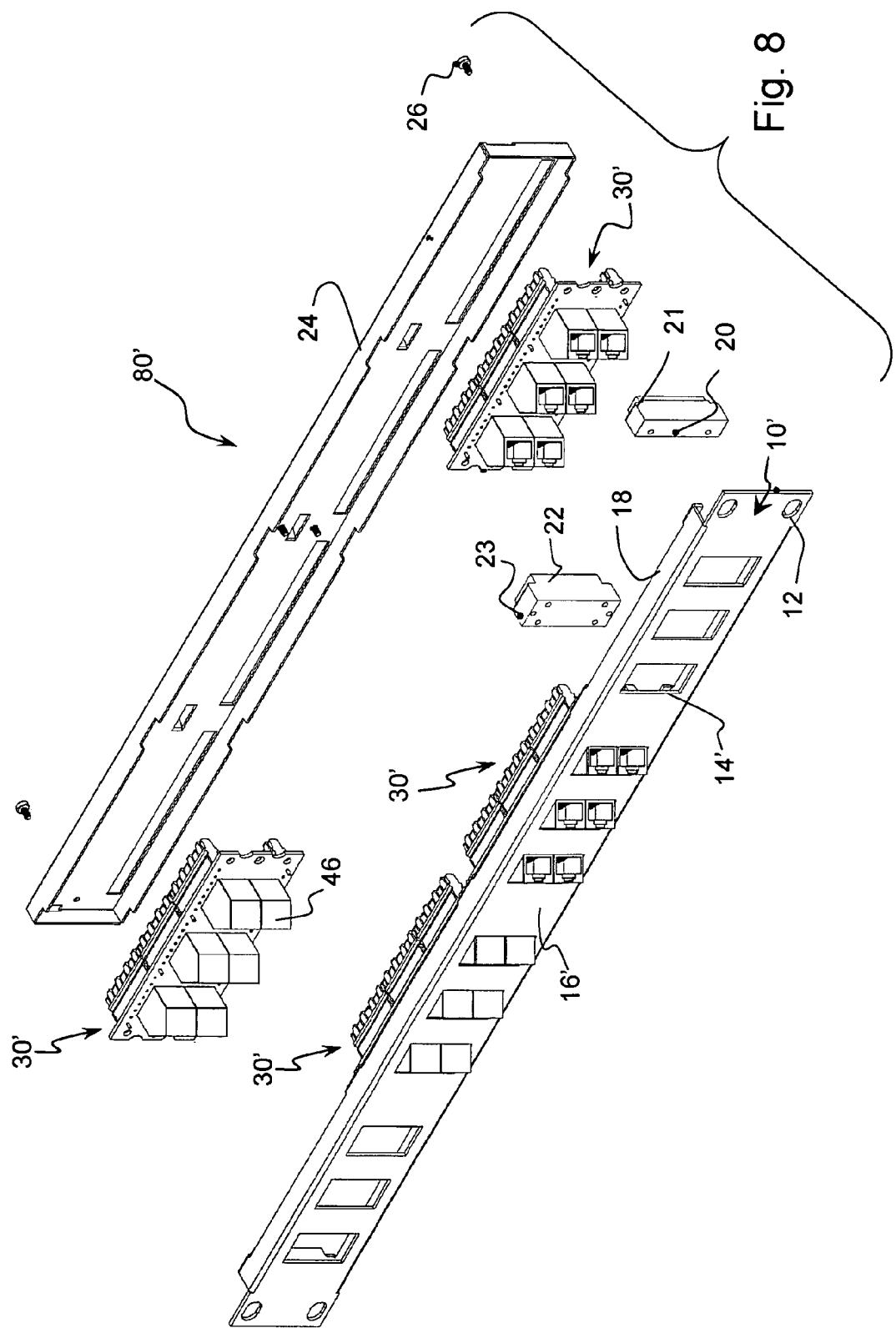

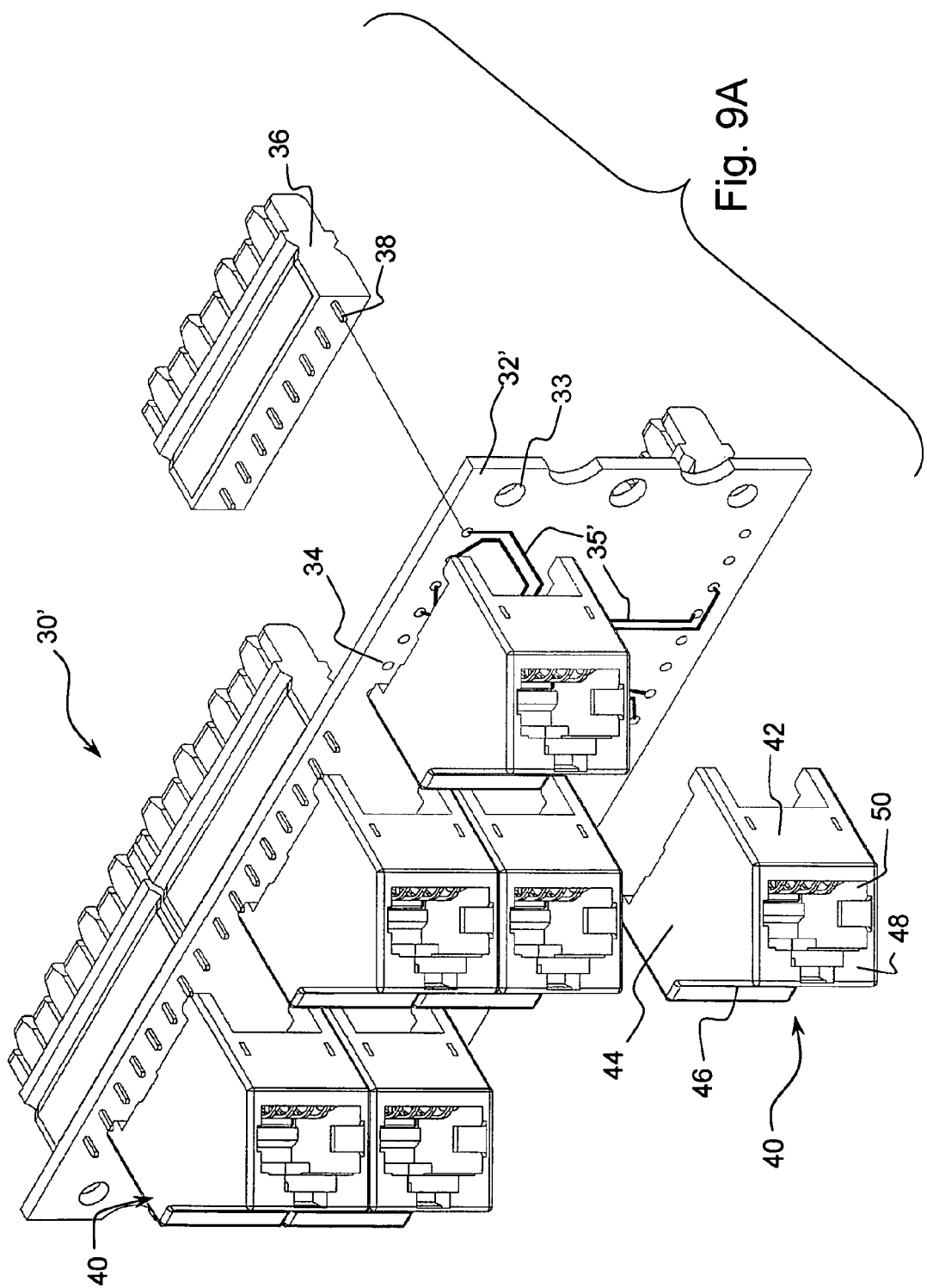

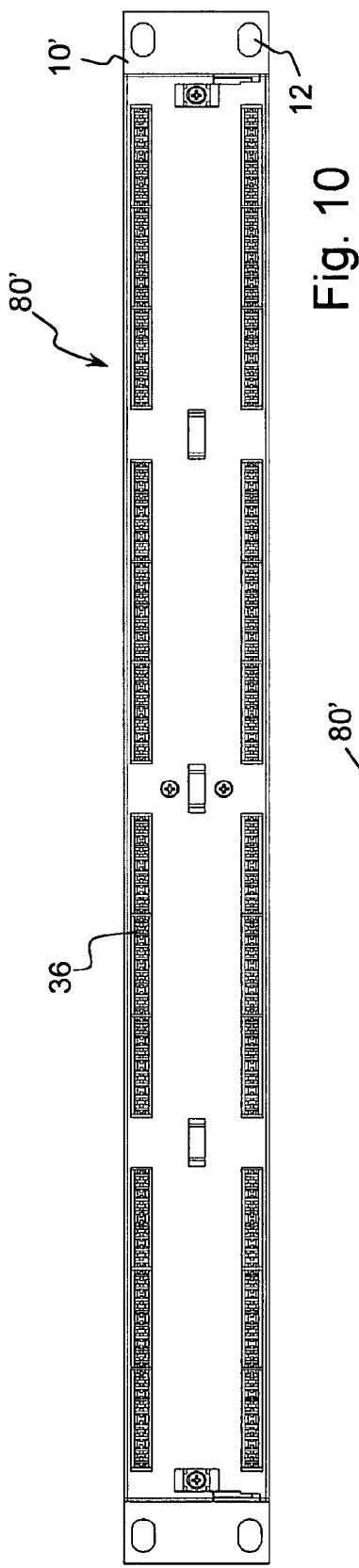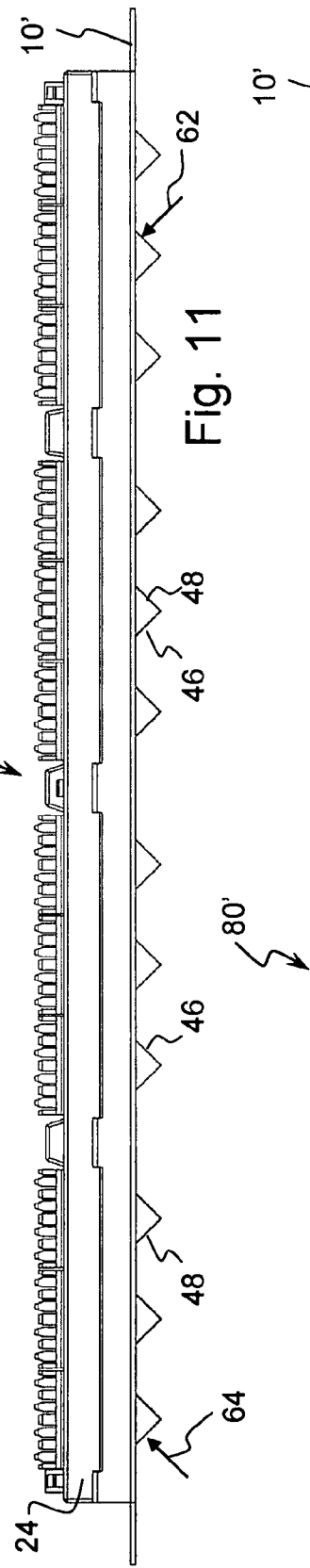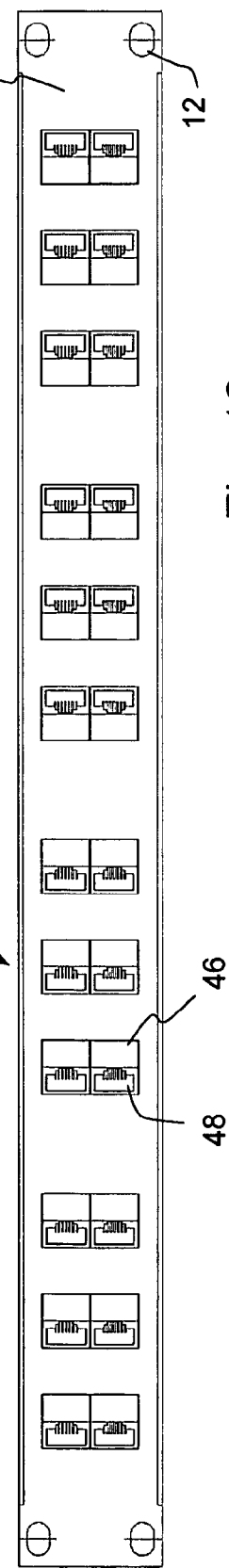

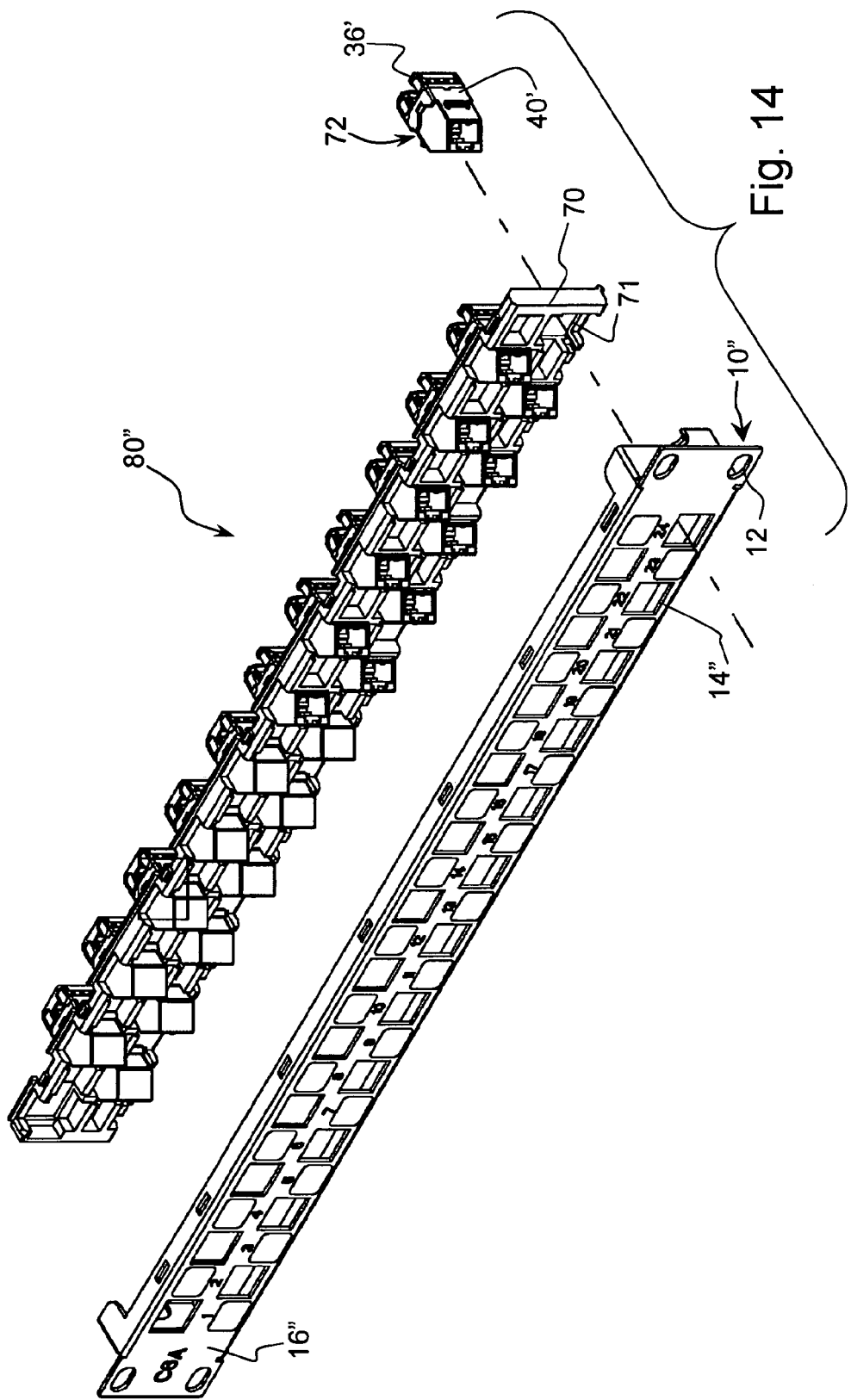

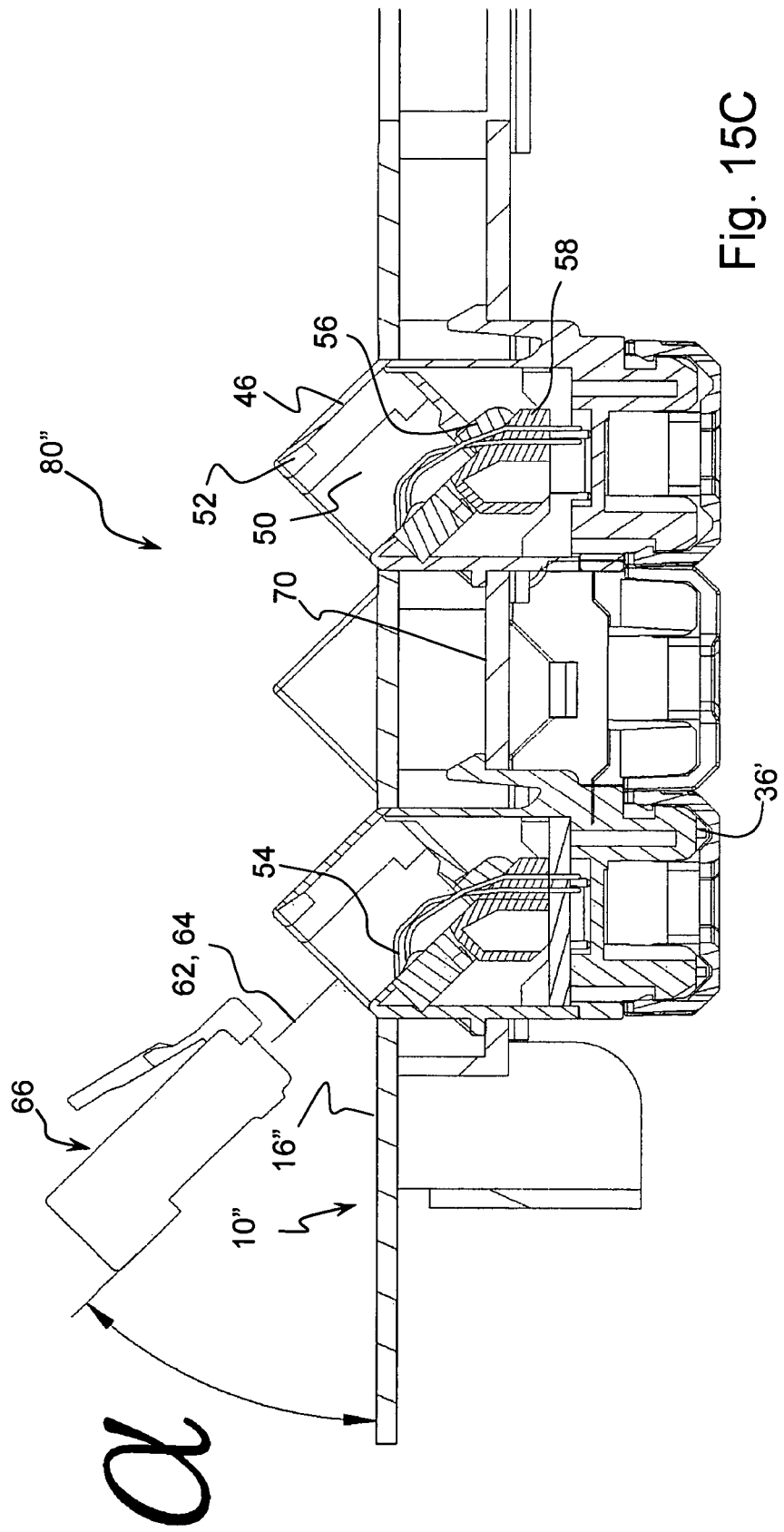

PATCH PANEL ASSEMBLY

FIELD OF THE INVENTION

The invention relates to a telecommunications patch panel assembly and more particularly to a patch panel with a frame having RJ module openings and a module assembly including a plurality of RJ jack portions that are accessed through the frame openings.

BACKGROUND OF THE INVENTION

Telecommunications patch panels have been provided that include a frame to support a plurality of RJ jacks and wire terminals (such as insulation displacement contact (IDC) terminals).

U.S. Pat. No. 6,273,752 discloses one type of patch panel design with a frame with openings wherein each opening receives an RJ jack module including a RJ plug receiving opening on one side and IDC terminals on an opposite side. A latching arrangement is provided for each RJ jack module to be connected to the frame and seated in alignment with a respective opening of the frame. U.S. Pat. No. 6,086,415 discloses a similar arrangement.

U.S. Pat. No. 6,504,726 discloses a patch panel with a plurality of RJ jack modules connected on each side of a circuit board. A telecommunications patch panel is provided including one or more modules mounted to the rear of a faceplate, each module with a circuit board including pairs of electrically linked connectors mounting on both sides of the circuit board held within the module by structure that holds the circuit board offset from the front and rear of the module with connectors accessible through a rear wall of the module and through the faceplate.

U.S. Pat. No. 6,736,670 discloses a patch panel including a plurality of electrical connector assemblies, wherein each of the electrical connector assemblies comprises a first jack presented on a first side of a panel frame of the patch panel and a second jack electrically linked to the first jack to form a jack pair and presented on a second side of the panel frame. Both the first jack and the second jack are presented at an angle with respect to the panel frame, and both the first jack and the second jack may be engaged using a patch cord. The first and second jack of each jack pair are at a 90-degree angle relative to one another.

U.S. Pat. No. 7,343,078 discloses a type of patch panel design with a frame with large openings and with a bezel mounted to the frame. The bezel has communication module openings that each receive a RJ jack module including a RJ plug receiving opening on one side and IDC terminals on an opposite side. A latching arrangement is provided for each RJ jack module to be connected to the frame and seated in alignment with a respective opening of the frame. The RJ jack module has a shape such that the RJ plug receiving opening is at an angle to the frame and to the bezel front surface. This allows RJ plugs to be connected with wires extending to the side.

SUMMARY OF THE INVENTION

According to the invention, a patch panel assembly is provided comprising an angle module including an RJ module with a base, an RJ plug receiving opening and spring contacts extending from the base into the RJ plug receiving opening, an insulation displacement contact (IDC) module including an IDC housing with an IDC module base and insulation displacement contacts (IDCs). The IDC contact pins extend from the IDC module base. A printed circuit board with RJ contact holes receives ends of the spring contacts with the RJ module mounted to the printed circuit board and with IDC contact holes receiving ends of the IDC contact pins with the IDC module mounted to the printed circuit board. The printed circuit board has circuit traces connecting the RJ contact holes to the IDC contact holes. The RJ plug receiving opening has a plug insertion opening at an angle to the printed circuit board between 0° and 90°. A front panel frame is provided including a front face with a plurality of RJ module openings. The angle module is connected to the frame with the RJ module extending through one of the RJ module openings, with the printed circuit board parallel to or nearly parallel to the front face of the front panel frame and with the plug insertion opening at an angle to the front face between 0° and 90°.

The frame may have the RJ module openings with two RJ modules extending therethrough. As an alternative each of the RJ module openings may have only one RJ module extending therethrough.

Each of the RJ module openings may be offset with respect to adjacent RJ module openings to provide the front face of the front panel frame on each side of each RJ module opening.

The RJ angle module may have a sloped first face and another sloped face defining the plug insertion opening. The RJ angle module may support the spring contacts so as to extend from the printed circuit board into the plug insertion opening of the RJ angle module and be positioned for contact with an RJ plug inserted into the plug insertion opening.

The angle module may have plural RJ modules mounted on the circuit board and plural IDC modules mounted on the circuit board and the circuit board is associated with plural RJ module openings of the front panel frame. Additional angle modules may be provided such that a plurality of angle modules are connected to the front panel frame. Each of the angle modules may include a circuit board with plural RJ modules mounted on the circuit board and plural IDC modules mounted on the circuit board. Each of the angle modules may be associated with plural RJ module opening of the front panel frame.

The angle module may have a single RJ module mounted on the printed circuit board with the angle module associated with a single RJ module opening. Additional angle modules may be provided such that a plurality of angle modules are connected to the front panel frame. Each of the angle modules may be associated with a respective RJ module opening of the front panel frame.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is an exploded view of a patch panel assembly according to the invention;

FIG. 2A is a partially exploded view of a module assembly according to the invention including RJ modules with angled RJ plug receiving opening, central circuit board and IDC modules;

FIG. 2C is a cross-sectional view showing the relationship of the mounted RJ angle modules, the printed circuit (PC) board and the surface plane of the panel frame for a first embodiment according to the invention wherein the same parallel relationship of surface panel to PC board is provided according to the second embodiment of the invention as well;

FIG. 4 is a rear view of the patch panel assembly according to the invention;

FIG. 5 is a side view of the patch panel assembly according to the invention;

FIG. 6 is a front view of the patch panel assembly according to the invention;

FIG. 8 is an exploded view of a patch panel assembly according to a second embodiment of the invention;

FIG. 9A is a partially exploded view of a module assembly according to another embodiment of the invention including RJ modules with angled RJ plug receiving opening, central circuit board and IDC modules;

FIG. 10 is a rear view of the patch panel assembly according to the second embodiment of the invention;

FIG. 11 is a side view of the patch panel assembly according to the second embodiment of the invention;

FIG. 12 is a front view of the patch panel assembly according to the second embodiment of the invention;

FIG. 14 is an exploded view of a patch panel assembly according to a third embodiment of the invention;

FIG. 15C is a side view showing the relationship of each angled keystone jack assembly to the front panel for the third embodiment according to the invention wherein the same parallel relationship of front panel to each PC board is provided;

DESCRIPTION OF THE PREFERRED EMBODIMENTS

Figure 2B:
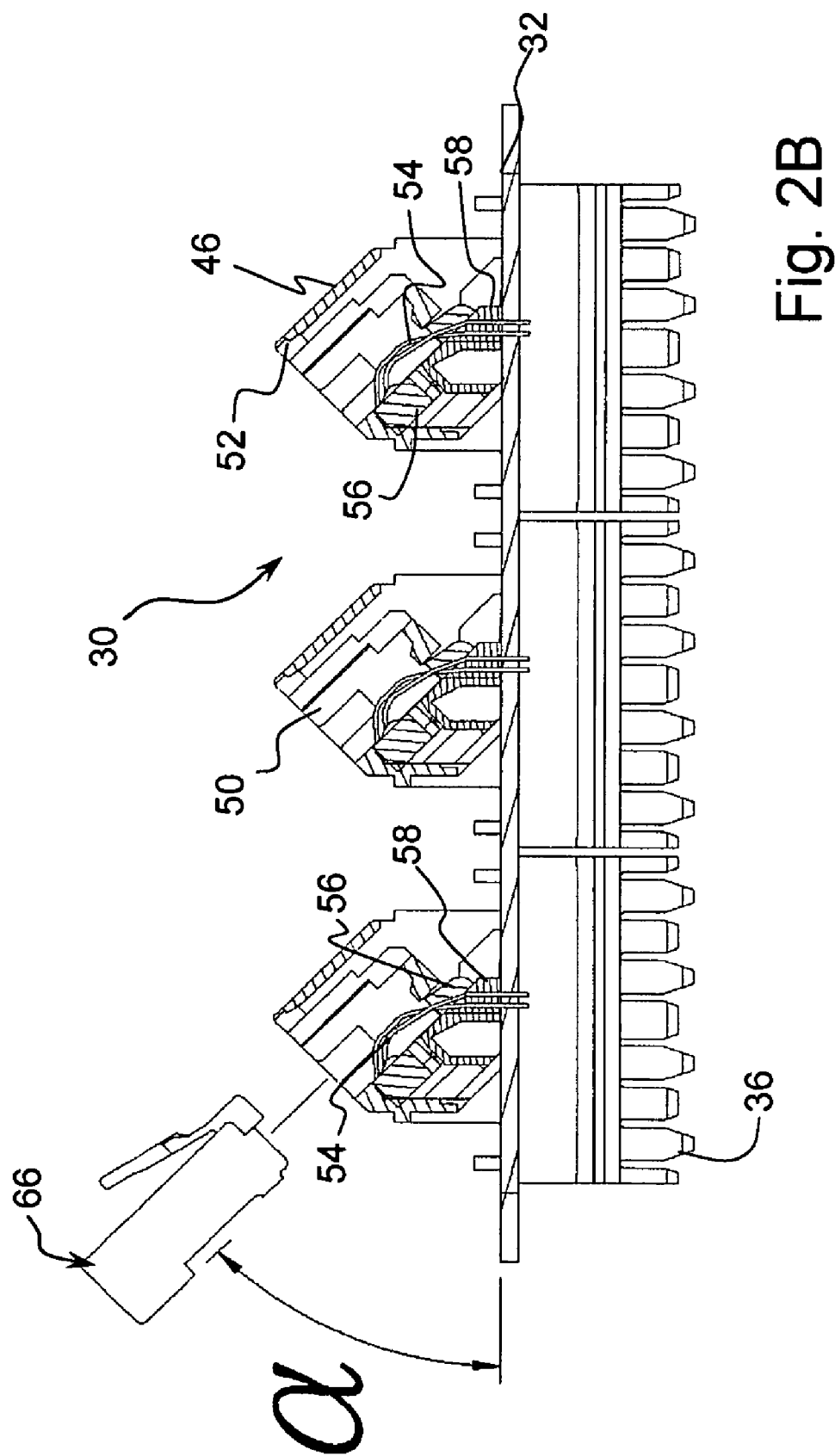
FIG. 2B is a cross-sectional view of an angle module assembly showing the interior of an RJ angle module mounted on a printed circuit board according to the invention.

Referring to the drawings in particular, FIG. 1 shows an exploded view of a first embodiment of a patch panel 80 according to the invention. The patch panel 80 comprises a front panel 10 with rack connection flange ends having openings 12 for connection to a standard rack structure. The front panel 10 has a front face 16 with a plurality of RJ module openings 14. The front panel 10 also has an upper and lower lip 18.

The patch panel 80 includes a plurality of angle module assemblies 30. As shown in FIG. 2A, each angle module assembly 30 includes a circuit board 32 with fastening openings 33 and with contact openings 34. A plurality of IDC housings 36 are provided each having insulation displacement contacts with protruding IDC pins 38. The insulation displacement contacts are aligned with slots in the housing 36 to terminate wires to the IDCs. Each IDC housing 36 is mounted on the respective circuit board 32 with pins 38 engaging perspective contact openings 34.

Each angle module assembly 30 includes a plurality of RJ jack angle modules 40. Each RJ jack angle module 40 has front to back surfaces 42 and side surfaces 44 with an angled edge to define angled surface 46 and angled plug opening surface 48. Each angled plug opening surface 48 defines an RJ plug opening 50. And in the edge of the RJ plug opening 50 there is a latching surface 52 for latching an RJ plug 66 that is inserted in an insertion direction 62, 64 that is essentially at a right angle to the plug opening surface 48.

FIG. 2B shows angle module assemblies 30 in cross-section. The IDC housings 36 are shown mounted on the circuit board 32. The RJ jack angle modules 40 are also mounted on the circuit board 32. Spring contacts 54 are supported by each RJ angle module 40 via an insert base 58 and an insert cover 56. This positions the spring contacts 54 for engagement by a RJ plug 66 as the RJ plug 66 is inserted into the RJ plug opening 50. With this construction, the RJ plug insertion directions 62 or 64 has an angle α that is less than 90° but greater than 0° with respect to the circuit board 32 (with respect to the plane of the circuit board 32). This is particularly illustrated in a cross-sectional view of FIG. 2C. FIG. 2C also shows the angle module assembly 38 seated and in a supported position with respect to the frame 10. In this seated position the printed circuit board 32 is parallel to the plane of the surface 16. In this case the angled RJ jack angle module 40 provides an RJ plug access opening 50 with an insertion direction axis 62, 64 that has an angle α with respect to the surface 16 of the panel frame 12.

Figure 3:
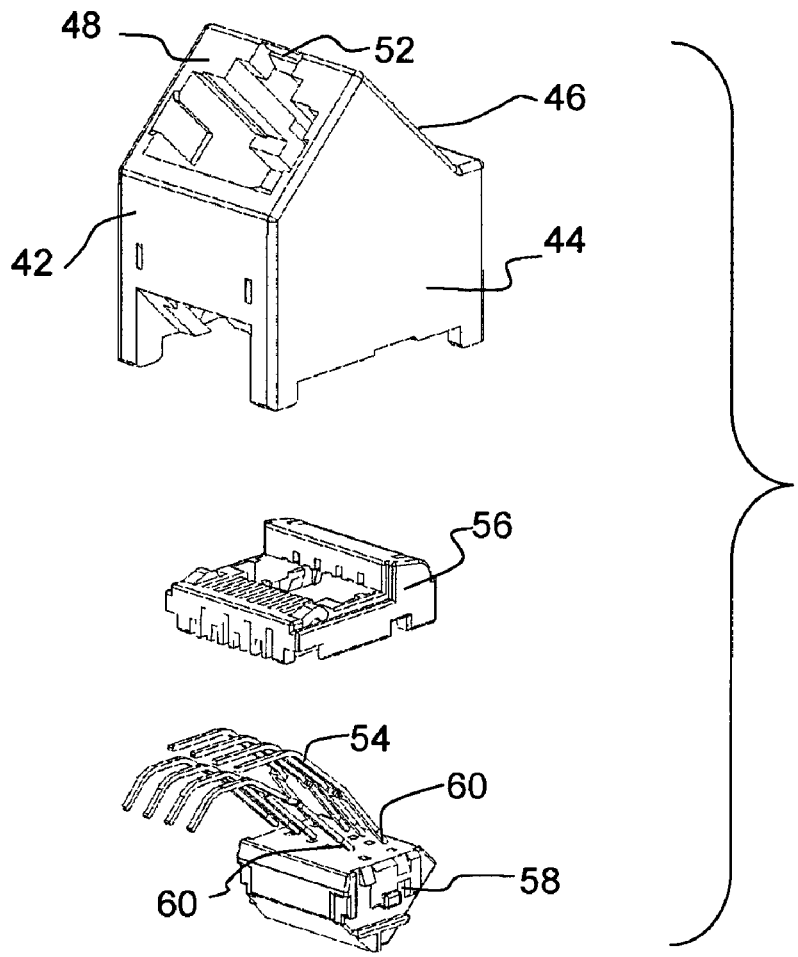
FIG. 3 is an exploded view of an RJ angle module used in both embodiments according to the invention.
Figure 7:
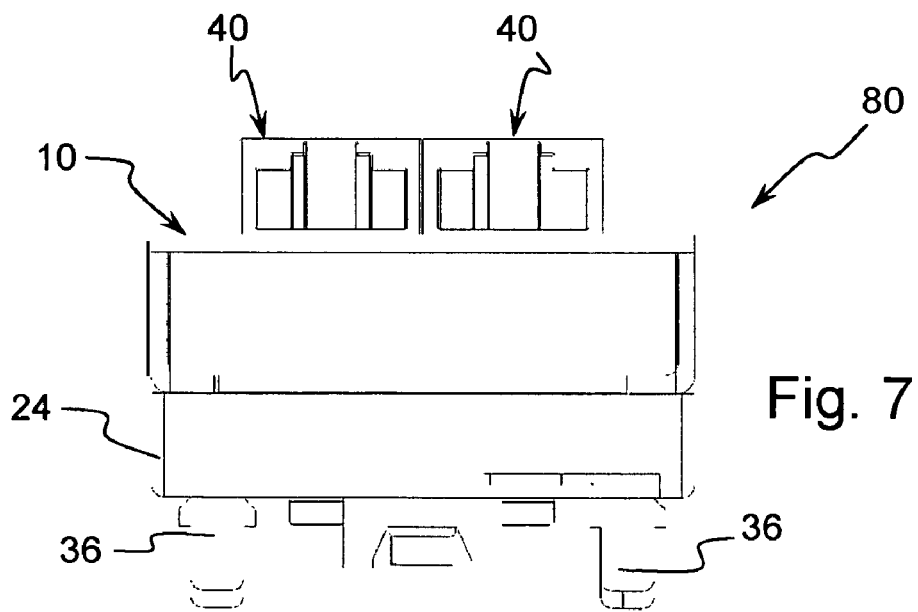
FIG. 7 is an end to view of the patch panel assembly according to the invention.

FIG. 3 shows an exploded view of the parts of the RJ jack angle modules 40. As can be seen in FIG. 3 the spring contacts 54 are inserted into the insert base 58. The insert base 58 with the spring contacts 54 mounted thereto and the insert cover 56 are connected to the housing with forward surface 42, side surfaces 44, angled surface 46, angled plug opening surface 48 etc. to form the RJ jack angle module 40. With this the spring contacts 54 are held in a spring contact position relative to the RJ jack opening 50. The spring contacts 54 have their ends inserted into the circuit board 32 via contact openings 34.

Each circuit board 32 includes circuitry 35 that provides a transmission path or the electrical interconnection between contact openings 34 connected to the IDC pins 38 and contact openings 34 connected to the spring contact pin ends 60. The circuitry 35 can also include reactive features (the inductive/capacitive) to reduce crosstalk and provide better transmission characteristics.

The front panel 10 is connected to and supports four angle module assemblies 30 with small support elements 20 and large support elements 22. Each small support element 20 is at an end of the assembly and connects an outermost angle module assemblies 30 to the front panel 10. Each large support element 22 is positioned between adjacent angle module assemblies 30. The support elements 20 and 22 are fixed to at the rear surface of the front panel 10. These small support elements 20 have a flange region 21 that extends underneath an edge of the upper and lower lip 18 to hold the small support elements 20 in position. In a similar manner, the large support elements 22 have a flange region 23 that extends underneath an edge of the upper and lower lip 18, to hold the large support elements 22 in position. The printed circuit board 32 of each angle module assemblies 30 has openings 33 which receives posts or fastening features of the support elements 20 and 22 to mount the module assemblies 30 to two large support elements or to a large support element and a small support element. In a mounted position the module assemblies 30 have a portion of each RJ jack angle module 40 extending through a respective RJ module openings 14 of the front panel 10. The patch panel 80 includes a back cover 24 which cooperates with the front panel and is connected by fasteners 26 to form a housing structure. The back cover 24 includes openings allowing wire access to the IDC modules 36 as can best be seen in FIG. 4.

As can be appreciated from FIG. 5, the RJ jack angle modules 40 are each positioned to either have a right to left component of the RJ plug insertion direction or to have a left to right component of the RJ plug insertion direction. In particular, as can be seen in FIGS. 5 and 6, the RJ jack angle modules 40 at the right side of the patch panel 80 have the angled plug opening surface 48 on the right with the angled surface 46 on the left to provide the right to left component of the RJ plug insertion direction 62. As can be seen in FIGS. 5 and 6 the RJ jack angle modules 40 on the left side of the patch panel 80 have angled plug opening surface 48 on the left with the angled surface 46 on the right to provide the left to right component of the RJ plug insertion direction 64.

FIG. 8 shows an exploded view of a second embodiment of the patch panel 80' according to the invention. The patch panel 80' includes a front panel 10' that is similar to the front panel 10 described above. The front panel 10' has side flanges 12 with openings for rack mounting as well as upper and lower front panel lips 18. The front panel 10' has a front face 16' with elongate openings 14', each for two RJ jack angle modules 40.

Figure 9B:
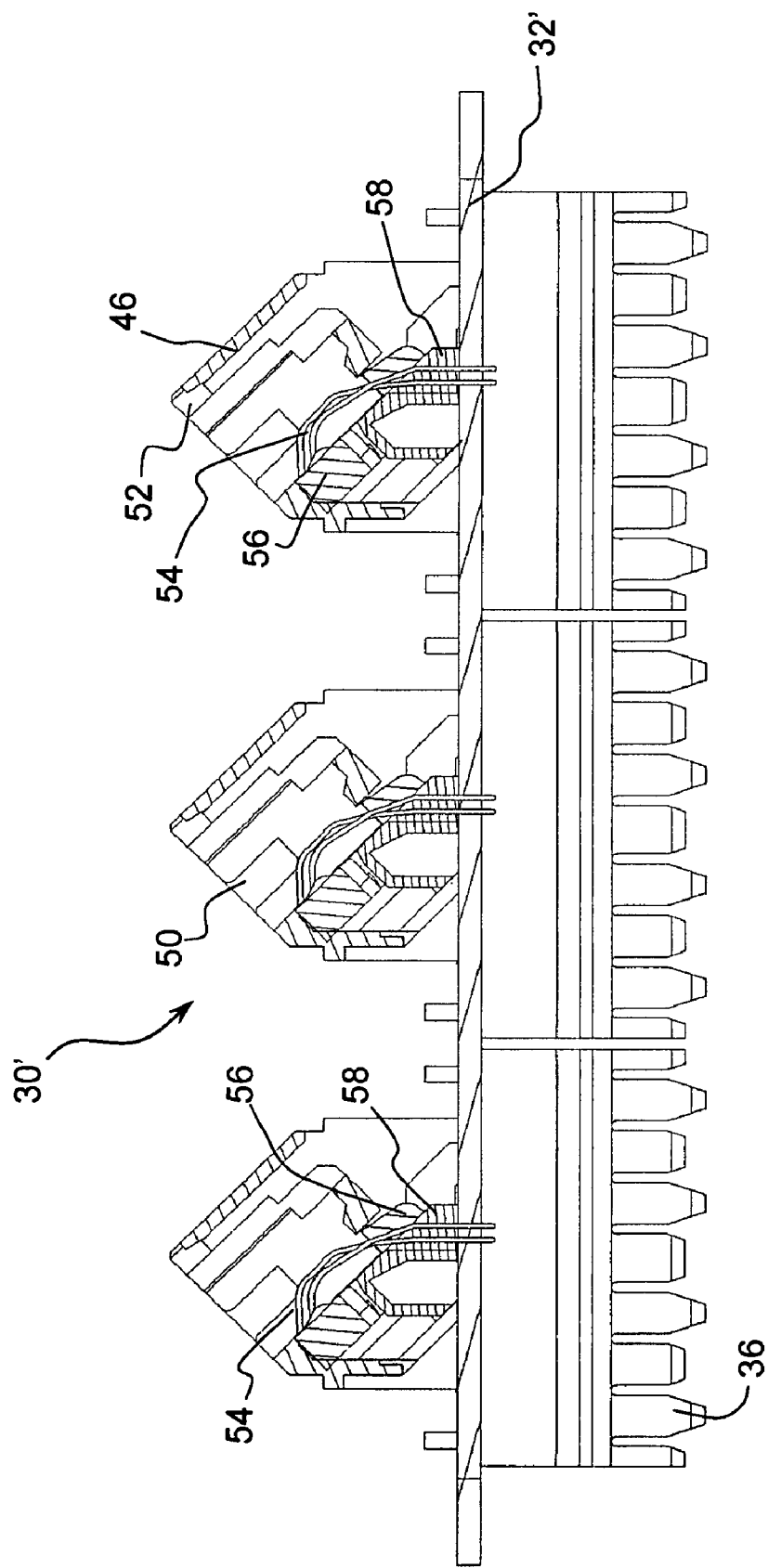
FIG. 9B is a cross-sectional view of an angle module assembly showing the interior of an RJ angle module mounted on a printed circuit board according to the invention.
Figure 13:
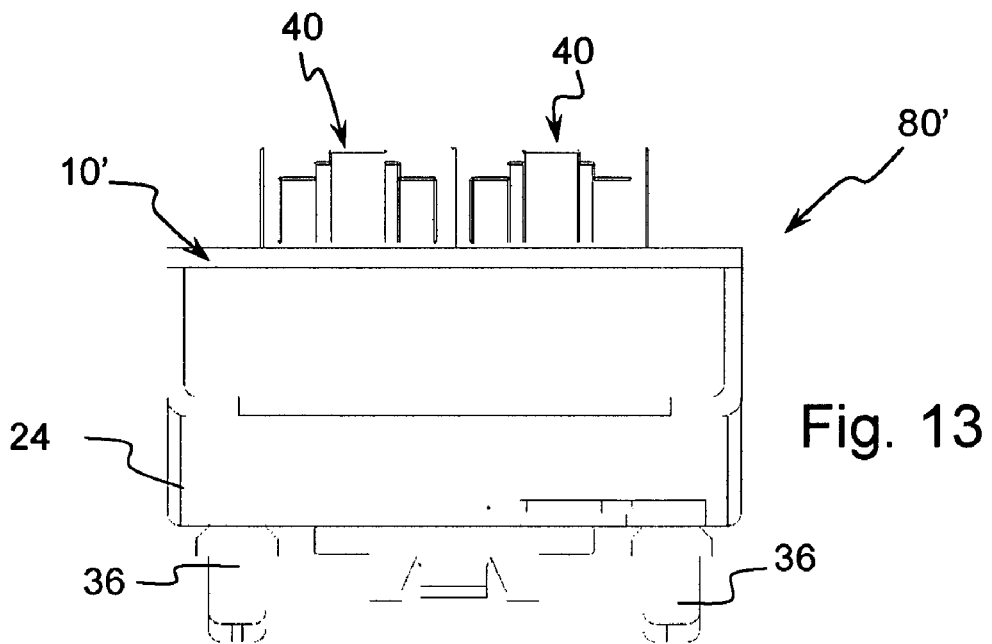
FIG. 13 is an end to view of the patch panel assembly according to the second embodiment of the invention.

The patch panel 80' has angle module assemblies 30' that are similar to those of the first embodiment. IDC modules 36 with the IDCs having pins 38 are mounted on a circuit board 32' that has contact openings 34 as well as fastening openings 33 (see FIG. 9A). Circuitry 35' is provided including transmission paths between the contact openings 34 for the IDCs and contact openings 34 for the spring contacts of the RJ jack angle modules 40. The RJ jack angle modules 40 are identical to those of the first embodiment. However, the modules 40 of the angle module assembly 30' are each mounted to the circuit board 32' so that they are provided in adjacent pairs as can be seen in FIG. 9A. As shown in FIGS. 11 and 12 the mounting of angle module assemblies 30' is such that the RJ jack angle modules 40 are each positioned to either have a right to left component of the RJ plug insertion direction 62 or to have a left to right component of the RJ plug insertion direction 64. In particular, as can be seen in FIGS. 11 and 12, the RJ jack angle modules 40 at the right side of the patch panel 80' have the angled plug opening surface 48 on the right with the angled surface 46 on the left to provide the right to left component of the RJ plug insertion direction 62. As can be seen in FIGS. 11 and 12 the RJ jack angle modules 40 on the left side of the patch panel 80' have angled plug opening surface 48 on the left with the angled surface 46 on the right to provide the left to right component of the RJ plug insertion direction 64.

FIG. 14 shows an angle patch panel assembly 80" according to a third embodiment of the invention. In a manner similar to the first and second embodiments, a front panel 10" is provided that includes a front face 16" with a plurality of RJ module openings 14. Further, an angle jack supporting frame 70 is provided that includes a plurality of Keystone jack support openings 71. Each opening 71 receives an angled Keystone jack 72.

Figure 15A:
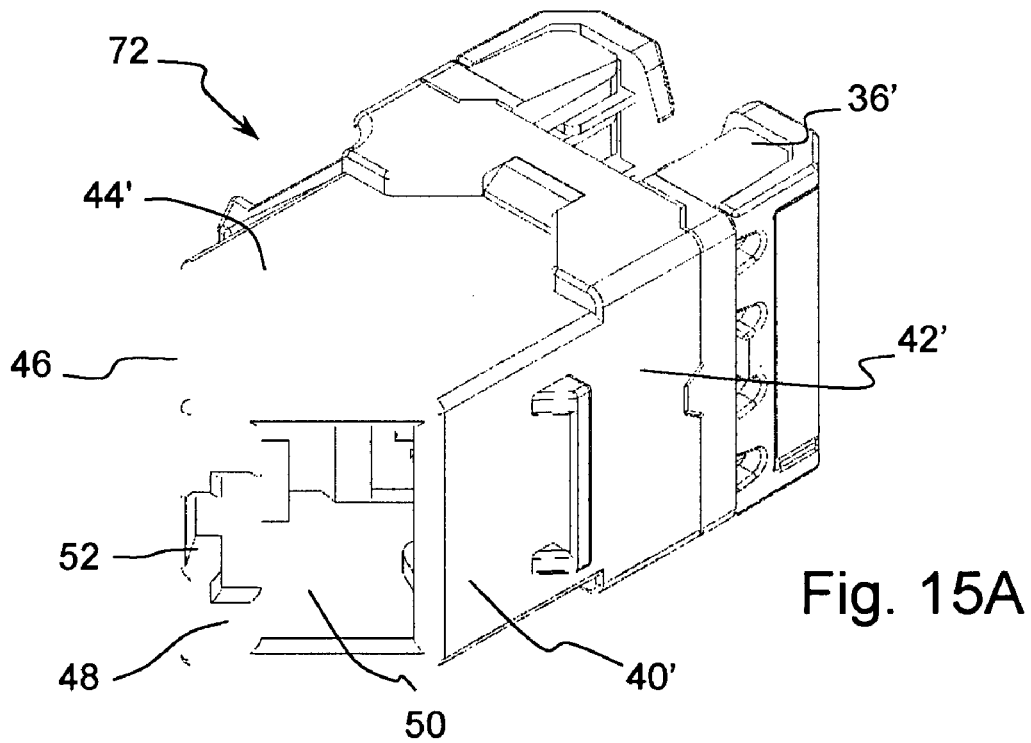
FIG. 15A is a perspective view of angled keystone jack assembly according to another embodiment of the invention.
Figure 15B:
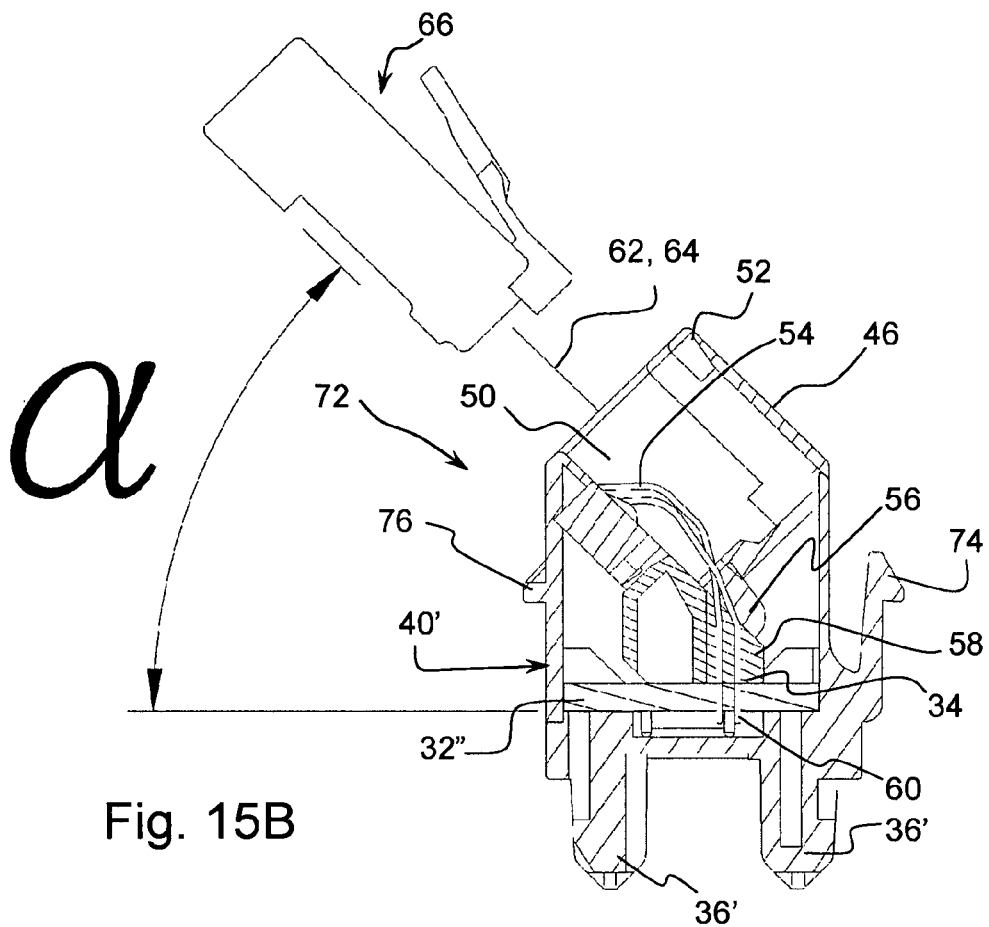
FIG. 15B is a cross-sectional view of the angled keystone jack assembly showing the interior of an RJ angle module mounted on a printed circuit board according to the third embodiment of the invention.
Figure 19:
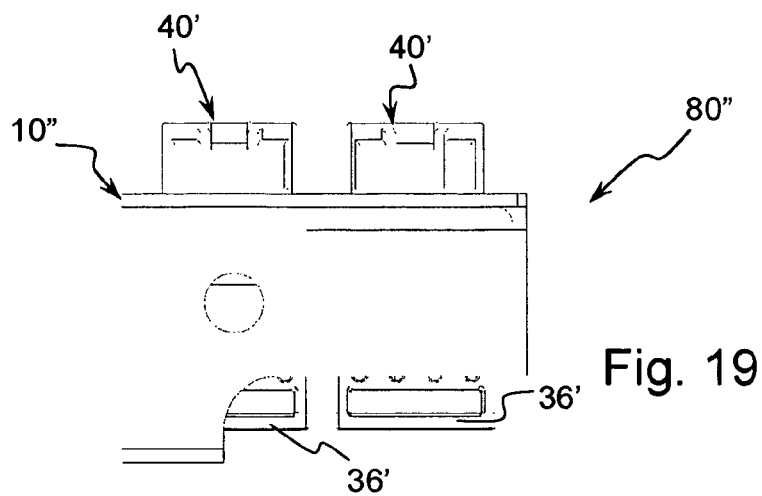
FIG. 19 is an end to view of the patch panel assembly according to the third embodiment of the invention.
Figure 16:
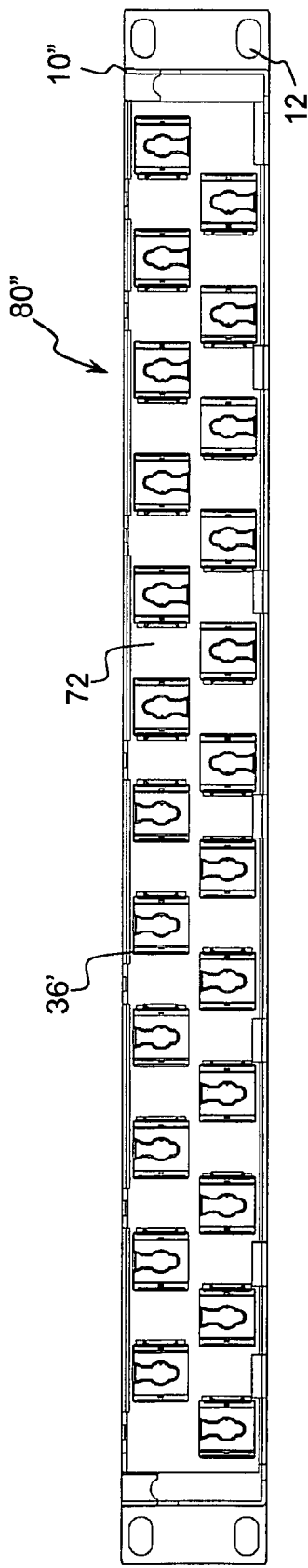
FIG. 16 is a rear view of the patch panel assembly according to the third embodiment of the invention.
Figure 17:
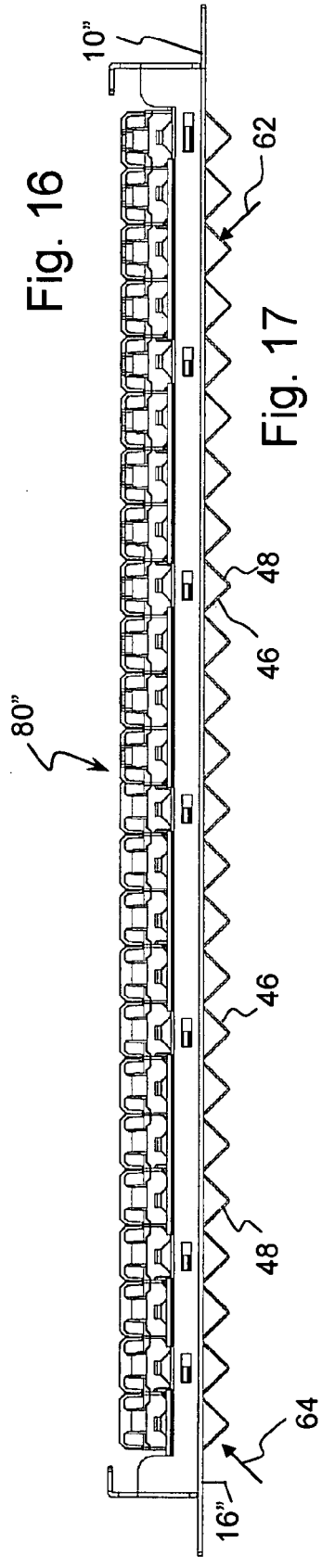
FIG. 17 is a side view of the patch panel assembly according to the third embodiment of the invention.
Figure 18:
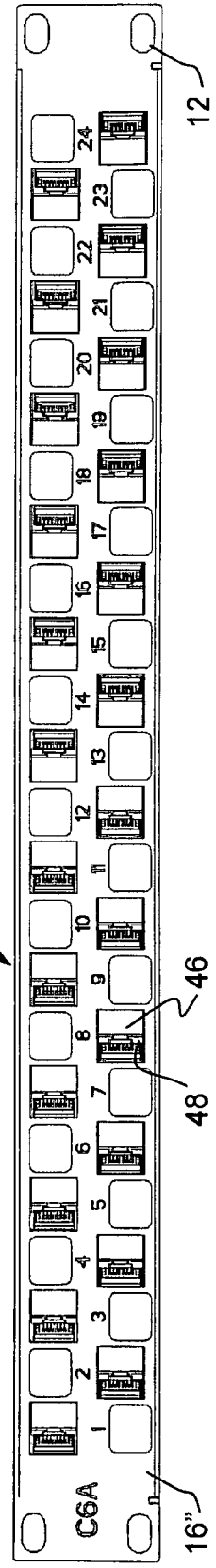
FIG. 18 is a front view of the patch panel assembly according to the third embodiment of the invention.

As can be seen in FIG. 15A, each angled Keystone jack 72 includes an RJ jack angle module 40', a printed circuit board 32" as well as IDC housings 36'. The RJ angle module 40' has a front and rear surface 42, sidewalls 44', an angled surface 46 as well as an angled plug opening surface 48 that provides the RJ plug opening 50. The RJ angle module 40' is mounted to the printed circuit board 32". IDC housings 36' have IDCs and are mounted to the printed circuit board 32" with pins of each IDC extending into contact openings 34 of a printed circuit board 32". Spring contacts ends 60 of spring contacts 54 extend into other contact openings 34 of printed circuit board 32". The spring contacts 54 are supported within the RJ angle module 40' via an insert base 58 and an insert cover 56. This positions the spring contacts 54 for engagement by a RJ plug 66 as the RJ plug 66 is inserted into the RJ plug opening 50. The exterior of each angled Keystone jack 72 has a stop surface 76 and a latch structure 74 allowing the angle jack supporting frame 70 to hold each angled Keystone jack 72 in a predefined position. The angle jack supporting frame 70, with the Keystone jack 72 in a seated and connected position is mounted on the front panel 10" such that the various circuit boards 32" are parallel or substantially parallel to the front face 16". The angled RJ jack module 40' provides an RJ plug access opening 50 with an insertion direction axis 62, 64 that has an angle $\alpha$ with respect to the surface 16 of the panel frame 12. With this construction, the RJ plug insertion directions 62 or 64 has an angle $\alpha$ that is less than 90° but greater than 0° with respect to the circuit board 32 (with respect to the plane of the circuit board 32) as shown in FIGS. 15B and 15C.

As shown in FIG. 15C, the arrangement provides the ability to have an RJ plug insertion direction 62 as well as an RJ plug insertion direction 64, based on the direction of connection of each angled Keystone jack 72 to the angle jack supporting frame 70. As each individual angled Keystone jack 72 can be removed and mounted independently, it is also possible to select any of the four directions for the plug insert direction for any particular angled Keystone jack 72.

While specific embodiments of the invention have been shown and described in detail to illustrate the application of the principles of the invention, it will be understood that the invention may be embodied otherwise without departing from such principles.

LIST OF REFERENCE NUMERALS 10 front panel (first embodiment)
10' front panel (second embodiment)
10" front panel (second embodiment)
12 rack connection flange with openings
14 RJ module openings (first embodiment)
14' RJ module openings (second embodiment)
14" RJ module openings (second embodiment)
16 front face (first embodiment)
16' front face (second embodiment)
18 front panel lip
20 small support element
22 large support element
24 back cover
26 fasteners
30 angle module assembly (first embodiment)
30' angle module assembly (second embodiment)
32 printed circuit board (first embodiment)
32' printed circuit board (second embodiment)
32" printed circuit board (third embodiment)

34 contact openings
35 circuitry
36 IDC housing
36' IDC housing of keystone jack assembly
38 IDC contact pins
40 RJ jack angle module
42 forward surface
44 side surface
46 angled surface
48 angled plug opening surface
50 RJ plug opening
52 latching surface
54 spring contacts
56 insert base
58 insert cover
60 spring contact ends
62 RJ plug insert direction (plug insertion axis)
64 RJ plug insert direction (plug insertion axis)
66 RJ plug with latch
70 angled jack supporting frame
72 angled keystone jack assembly
74 angled keystone jack latch
76 angled keystone jack stop surface
80 patch panel assembly (first embodiment)
80' patch panel assembly (second embodiment)
80" patch panel assembly (third embodiment)

What is claimed is:

1. A patch panel assembly comprising:
an angle module including an RJ module with a base, an RJ plug receiving opening and spring contacts extending from said base into said RJ plug receiving opening, an insulation displacement contact (IDC) module including an IDC housing with an IDC module base and insulation displacement contacts (IDCs) with IDC contact pins extending from said IDC module base and a printed circuit board with RJ contact holes receiving ends of said spring contacts with said RJ module mounted to said printed circuit board and with IDC contact holes receiving ends of said IDC contact pins with said IDC module mounted to said printed circuit board and with circuit traces connecting said RJ contact holes to said IDC contact holes, said RJ plug receiving opening having a plug insertion opening at an angle to said printed circuit board between 0° and 90°; and
a front panel frame including a front face with a plurality of RJ module openings, said angle module being connected to said frame with said RJ module extending through one of said RJ module openings, with said printed circuit board parallel to or nearly parallel to said front face of said front panel frame and with said plug insertion opening at an angle to said front face between 0° and 90°.

2. A patch panel assembly according to claim 1, wherein each of said RJ module openings has two RJ modules extending therethrough.

3. A patch panel assembly according to claim 1, wherein each of said RJ module openings has only one RJ module extending therethrough.

4. A patch panel assembly according to claim 3, wherein each of said RJ module openings is offset with respect to adjacent RJ module openings to provide said front face of said front panel frame on each side of each RJ module opening.

5. A patch panel assembly according to claim 1, wherein said RJ angle module has a sloped first face and another sloped face defining said plug insertion opening.

6. A patch panel assembly according to claim 5, wherein said RJ angle module supports said spring contacts so as to extend from said printed circuit board into said plug insertion opening of said RJ angle module and be positioned for contact with an RJ plug inserted into said plug insertion opening.

7. A patch panel assembly according to claim 1, wherein said angle module has plural RJ modules mounted on said circuit board and plural IDC modules mounted on said circuit board and said circuit board is associated with plural RJ module openings of said front panel frame.

8. A patch panel assembly according to claim 7, further comprising additional angle modules, to provide a plurality of angle modules connected to said front panel frame, each of said angle modules including a circuit board with plural RJ modules mounted on said circuit board and plural IDC modules mounted on said circuit board, each of said angle modules being associated with plural RJ module opening of said front panel frame.

9. A patch panel assembly according to claim 1, wherein said angle module has a single RJ module mounted on said printed circuit board with said angle module associated with a single RJ module opening.

10. A patch panel assembly according to claim 9, further comprising additional angle modules to provide a plurality of angle modules connected to said front panel frame, with each of said angle modules being associated with a respective RJ module opening of said front panel frame.

* * * * *